US006193873B1

(12) United States Patent
Ohara et al.

(10) Patent No.: US 6,193,873 B1
(45) Date of Patent: Feb. 27, 2001

(54) SAMPLE DETECTION TO INITIATE TIMING OF AN ELECTROCHEMICAL ASSAY

(75) Inventors: Timothy J. Ohara, San Ramon; Maria Teodorczyk, San Jose; Mahyar Z. Kermani, Pleasanton, all of CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 09/333,793

(22) Filed: Jun. 15, 1999

(51) Int. Cl.[7] .................................................... G01N 27/26

(52) U.S. Cl. ....................... 205/792; 205/777.5; 205/775; 204/400; 204/406; 204/403

(58) Field of Search ................................ 205/775, 777.5, 205/792; 204/400, 406, 403

(56) References Cited

U.S. PATENT DOCUMENTS

| | | | |
|---|---|---|---|
| 4,224,125 | 9/1980 | Nakamura et al. | 128/195 |
| 4,545,382 | 10/1985 | Higgins et al. | 128/635 |
| 4,940,945 | 7/1990 | Littlejohn et al. | 324/438 |
| 5,266,179 | 11/1993 | Nankai et al. | 204/401 |
| 5,366,609 | 11/1994 | White et al. | 204/407 |

FOREIGN PATENT DOCUMENTS

| | | |
|---|---|---|
| 148387 | 12/1979 | (DE) . |
| 208230 | 11/1981 | (DE) . |

*Primary Examiner*—T. Tung
*Assistant Examiner*—Alex Noguerola
(74) *Attorney, Agent, or Firm*—James Riesenfeld

(57) ABSTRACT

An electrochemical assay includes a method for determining with great accuracy the time at which an applied sample bridges a gap between the electrodes of an electrochemical cell. The method involves applying a constant small current across the gap, while monitoring the potential difference between the electrodes. The time at which the sample bridges the gap is marked by a sharp drop in the potential. A constant voltage is applied after the sample is detected, and the current and/or charge through the sample is monitored over a period of time. From the measured current or charge, the analyte concentration of interest can be calculated.

15 Claims, 6 Drawing Sheets

V+

101
102
103
V1
104
109
105
107
108
1
2
S
V2
110
111
112
106

SAMPLE DETECTION TO INITIATE TIMING OF AN ELECTROCHEMICAL ASSAY

BACKGROUND OF THE INVENTION

1. Field of the Invention

This invention relates to an electrochemical device for measuring the concentration of an analyte in a biological fluid; more particularly, to a mechanism for determining the time at which the fluid provides an electrical connection between working and reference electrodes of the device.

2. Description of the Related Art

A variety of medical diagnostic procedures involve tests on biological fluids, such as blood, urine, or saliva, to determine an analyte concentration in the fluid. Among the analytes of greatest interest is glucose, and dry phase reagent strips incorporating enzyme-based compositions are used extensively in clinical laboratories, physicians, offices, hospitals, and homes to test samples of biological fluids for glucose concentration. In fact, reagent strips have become an everyday necessity for many of the nation's estimated 16 million people with diabetes. Since diabetes can cause dangerous anomalies in blood chemistry, it can contribute to vision loss, kidney failure, and other serious medical consequences. To minimize the risk of these consequences, most people with diabetes must test themselves periodically, then adjust their glucose concentration accordingly, for instance, through diet control and/or with insulin injections. Some patients must test their blood glucose concentration as often as four times or more daily.

It is especially important for people with diabetes who must control their diet in order to regulate sugar intake and/or administer insulin injections, and who must be guided in this regard by frequent tests of blood glucose concentration, to have a rapid, inexpensive, and accurate system for glucose determination.

One type of glucose measurement system operates electrochemically, detecting the oxidation of blood glucose on a dry reagent strip. The reagent generally includes an enzyme, such as glucose oxidase or glucose dehydrogenase, and a redox mediator, such as ferrocene or ferricyanide. This type of measurement system is described in U.S. Pat. No. 4,224,125, issued on Sep. 23, 1980, to Nakamura et al.; U.S. Pat. No. 4,545,382, issued on Oct. 8, 1985, to Higgins et al.; and U.S. Pat. No. 5,266,179, issued on Nov. 30, 1993, to Nankai et al., incorporated herein by reference.

Electrochemical glucose meters can be characterized as coulometric, amperometric, or potentiometric, depending on whether the system involves measuring charge, current, or potential, respectively, in making the determination of glucose concentration. In each case, it is important to define the point in time when the blood sample contacts the reagent, since an electrical signal must be applied to the strip at a precisely timed period thereafter.

Nankai et al., U.S. Pat. No. 5,266,179, issued on Nov. 30, 1993, discloses an electrochemical system for measuring blood glucose, in which the sample application time is defined as the time of a resistance drop between a pair of electrodes to which a constant voltage was applied.

White et al., U.S. Pat. No. 5,366,609, issued on Nov. 22, 1994, describes the same principle of monitoring the resistance drop between the electrodes to determine the time at which blood was applied to a dry glucose reagent strip. In both patents, a constant voltage is applied between working and reference electrodes to track resistance changes that result from the introduction of a blood sample to a dry reagent strip.

For accurate results, the sample detection procedure should not perturb the analyte concentration, and several techniques for minimizing analyte perturbation have been described.

Quade et al., German (DDR) Patent Application 148,387, filed on Dec. 28, 1979, discloses an electrochemical measurement that uses a novel electronic circuit, which allows rapid switching between potentiostatic (constant applied voltage) and galvanostatic (constant applied current) modes, while also allowing a reduction in the number of electronic components. A goal of the circuit is to minimize perturbation of the sample before the start of a measurement.

Bartels et al., German (DDR) Patent Application 208,230, filed on Nov. 24, 1981, discloses an electrochemical measurement that also attempts to minimize sample perturbation. The measurement device includes a circuit that uses a diode to minimize current flow before the start of the measurement, without using an additional amperometric control loop. Furthermore, the circuit switches to the potentiometric mode in a precise and rapid fashion.

Littlejohn et al., U.S. Pat. No. 4,940,945, issued on Jul. 10, 1990, discloses a portable apparatus that can measure the pH of a blood sample. The apparatus detects the presence of a sample in a cell by injecting a constant current between a fill electrode outside the sample chamber and one of two electrodes inside the chamber. When the impedance decreases by at least two orders of magnitude, the meter recognizes that sufficient sample has been provided and emits a beep. The fill electrode is then cut out of the circuit that includes the two electrodes inside the sample cell, and measurements are made potentiometrically.

SUMMARY OF THE INVENTION

The present invention provides a method for measuring an analyte concentration in a sample of a biological fluid that is applied to an electrochemical diagnostic strip of the type that includes juxtaposed working and reference electrodes. The method comprises:

(a) applying a predetermined, constant current source between the working and reference electrodes, (b) monitoring a potential difference across the electrodes, (c) applying the sample to the strip, (d) determining a sample detection time by noting when the potential difference falls below a predetermined threshold voltage, (e) applying a predetermined constant voltage to the sample, (f) measuring an electrical response at a predetermined time after applying the constant voltage, and (g) calculating the analyte concentration, using the measured electrical response.

A meter for measuring an analyte concentration in a sample of a biological fluid that has been applied to a diagnostic strip comprises, in electrical communication, (a) means for applying a predetermined current between the working and references electrodes, (b) means for monitoring a potential difference across the electrodes, (c) means for determining when the potential difference falls below a predetermined threshold voltage to indicate sample detection, (d) means responsive to sample detection for applying a predetermined constant voltage to the sample, (e) means for measuring a resulting electrical response, and (f) means for calculating the analyte concentration by using the measured electrical response.

The present invention provides a method and apparatus for measuring analyte concentration electrochemically, which includes defining with great accuracy the time at which a sample that is applied to the reaction zone of an electrochemical diagnostic strip bridges the gap between the electrodes. Determining the sample application time (more precisely, the sample detection time; we use the terms interchangeably) accurately permits greater accuracy and precision of the assay done on the sample.

An advantage of the present method for determining sample application time is that applying a constant, small current for detecting sample minimizes sample perturbation, compared with prior art methods that applied a constant voltage. Using the latter approach, applying a sample causes a current that exceeds a defined threshold to initiate timing. Since the sampling rate is limited, the current will typically be substantial, before the sensor recognizes that the threshold has been exceeded. When a large current is observed, a correspondingly large perturbation in the mediator is observed. This could lead to an inaccurate measurement, especially at low analyte concentrations.

The prior art method of applying a constant potential to detect sample application has another disadvantage in that the initial current generally decreases with decreasing analyte concentration. Thus it is more difficult to determine an initial sample detection time for low-analyte samples. By the same token, if the current threshold is set too low, it can be falsely triggered by noise. To further complicate matters, the presence of a high concentration of red blood cells also decreases the initial current.

Analyte and red blood cell concentrations do not affect the method of the present invention. Likewise, noise is not a significant problem either, because the detection trigger is a large change in signal voltage.

DETAILED DESCRIPTION OF THE INVENTION

This invention relates to an electrochemical method of measuring an analyte concentration in a biological fluid. In the interest of brevity, the description below emphasizes measuring glucose concentration in samples of whole blood; however, the person of ordinary skill in the medical diagnostics art will recognize how the description can be adapted to monitor other analytes (such as cholesterol, ketone bodies, alcohol, etc.) in other fluids (such as saliva, urine, interstitial fluid, etc.)

The electrochemical (amperometric) method for measuring an analyte concentration in an aqueous sample involves placing the sample into a reaction zone in an electrochemical cell that has two electrodes having an impedance that is suitable for the amperometric measurement. The analyte is allowed to react directly with an electrode or with a redox reagent to form an oxidizable (or reducible) substance in an amount that corresponds to the analyte concentration. The quantity of oxidizable (or reducible) substance is then determined electrochemically. This type of assay must accurately define the point in time at which the sample is detected in the reaction zone. This permits an electrochemical waveform (i.e., voltage) to be applied immediately after the sample has been applied and accurately defines an incubation period or reaction time. In turn, this improves the accuracy and precision of the assay, as described below.

The present invention provides an improved method and apparatus for determining the sample detection time. The method involves applying a small, constant current source across the electrode of an electrochemical diagnostic strip and monitoring the potential difference between the electrodes. Since there is a dry gap between the electrodes, negligible current flows initially. When sample is applied to the strip and fills the gap, the measured voltage decreases rapidly, causing the test time to be initiated. On thus recognizing that sample has been applied, the apparatus switches from a constant current to constant voltage mode. In the constant voltage mode, either current or charge are measured as a function of time to permit the analyte concentration to be calculated. This technique minimizes the error introduced into signal response by the timing-initiation circuit and thereby enables low detection limits. The electronic components are simple and inexpensive.

Figure 1:
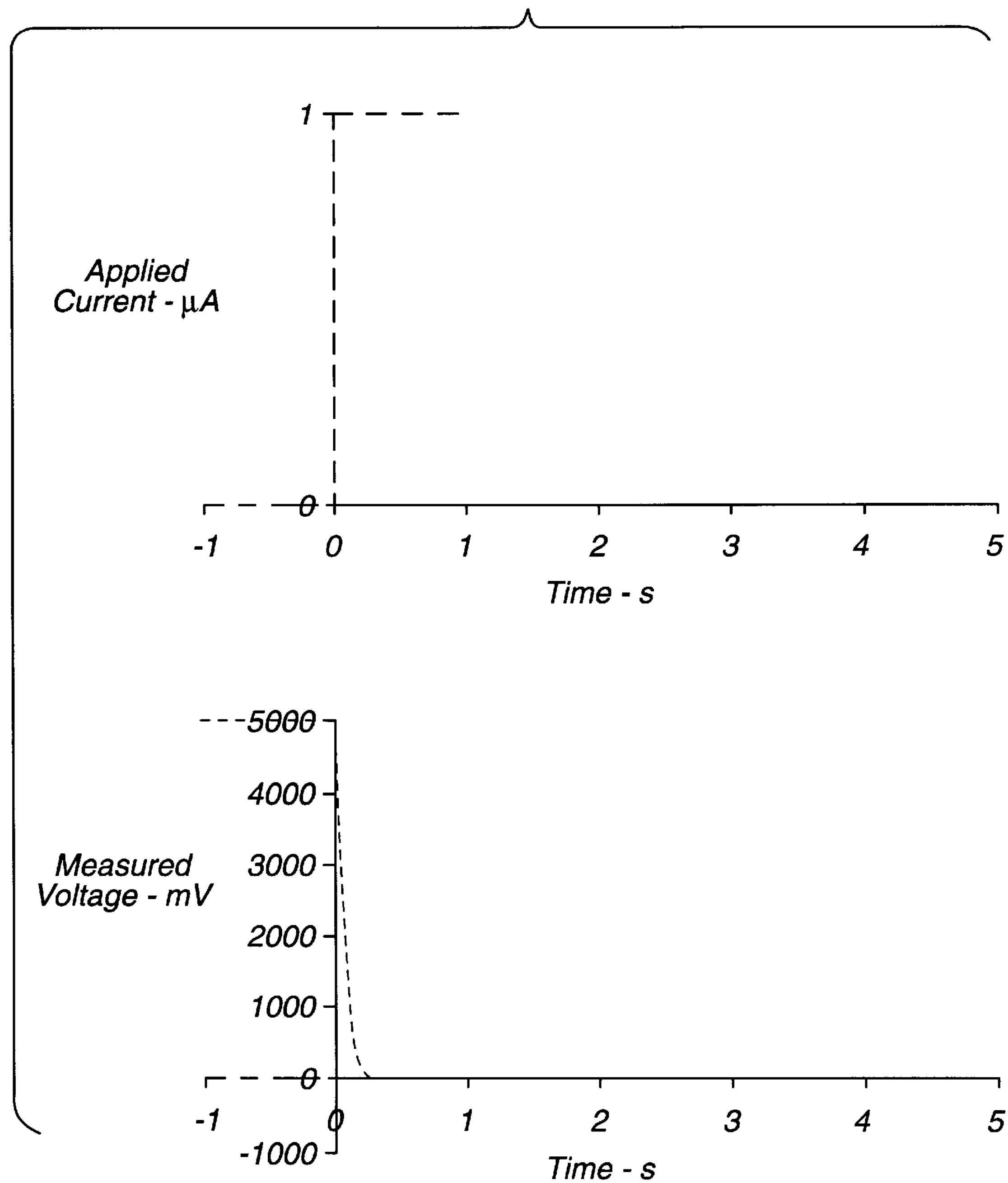
FIG. 1 is a graph of applied current and measured voltage vs. time that depicts the sample-detection process of the present invention.

FIG. 1 is a plot of applied current and measured voltage that depicts the sample-detection process of the present invention. Prior to time zero (i.e., before sample is introduced), a constant (here, for example 1 $\mu$A) current is applied between the electrodes, but negligible current flows. Smaller current reduces perturbation and is preferred, particularly for small analyte concentration. The measured voltage is determined by the circuit power supply voltage—in this case, 5 volts. When the sample is introduced into the cell (at time zero), the applied current can flow between the electrodes and the measured voltage falls rapidly. When the voltage falls below a threshold voltage, the device switches from constant applied current to constant applied voltage.

Figure 2:
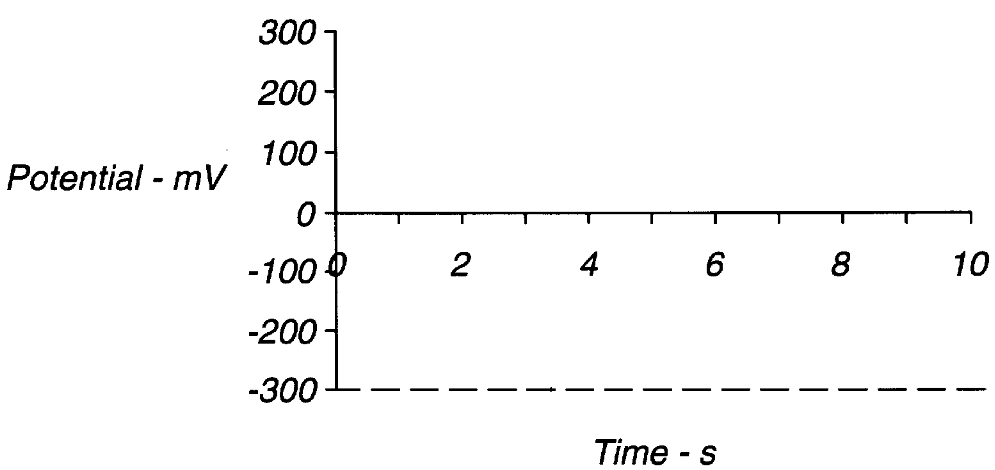
FIG. 2 is a graph of applied voltage and resulting current response vs. time for an assay method of the present invention.
Figure 2:
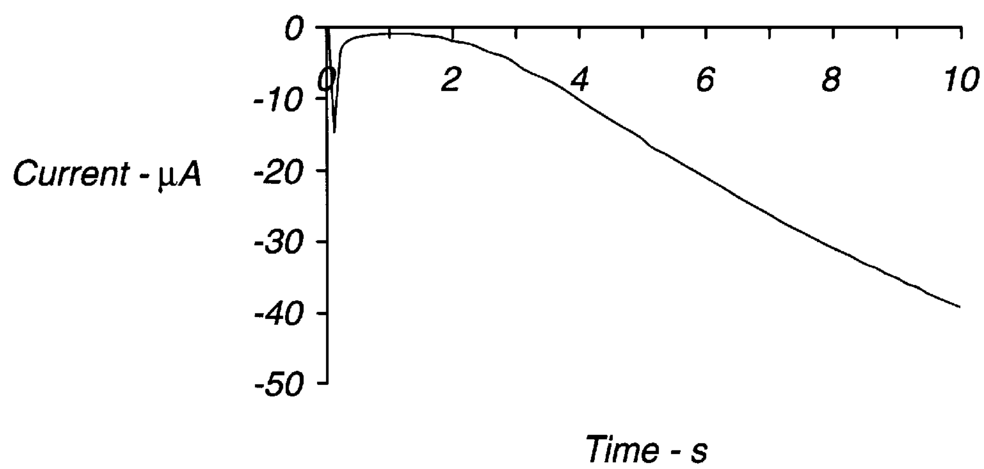

FIG. 2 is a graph that depicts the applied potential and measured current as a function of time after sample detection. Sample is detected at time t=0, and a voltage is applied between the working and counter electrodes immediately thereafter. As a result, current flows between the electrodes. The current after a predetermined time is a measure of the analyte concentration, once the system has been calibrated, using samples having known analyte concentrations. The duration of the predetermined time is not critical. It is generally at least about 3 seconds when the fluid is blood and the analyte is glucose. That duration generally provides sufficient time to dissolve reagents and reduce an amount of mediator that is readily measurable. All things being equal, at high hematocrit, longer times are needed. Practically speaking, a user is generally interested in having a reading as soon as possible. Ten seconds duration is typically satisfactory, with no motivation to wait longer. Of course, once a predetermined time is set, accurate and precise results require that the same time be used each time. In any case, the accuracy of the current determination depends on the accuracy of the t=0 determination.

Figure 3:
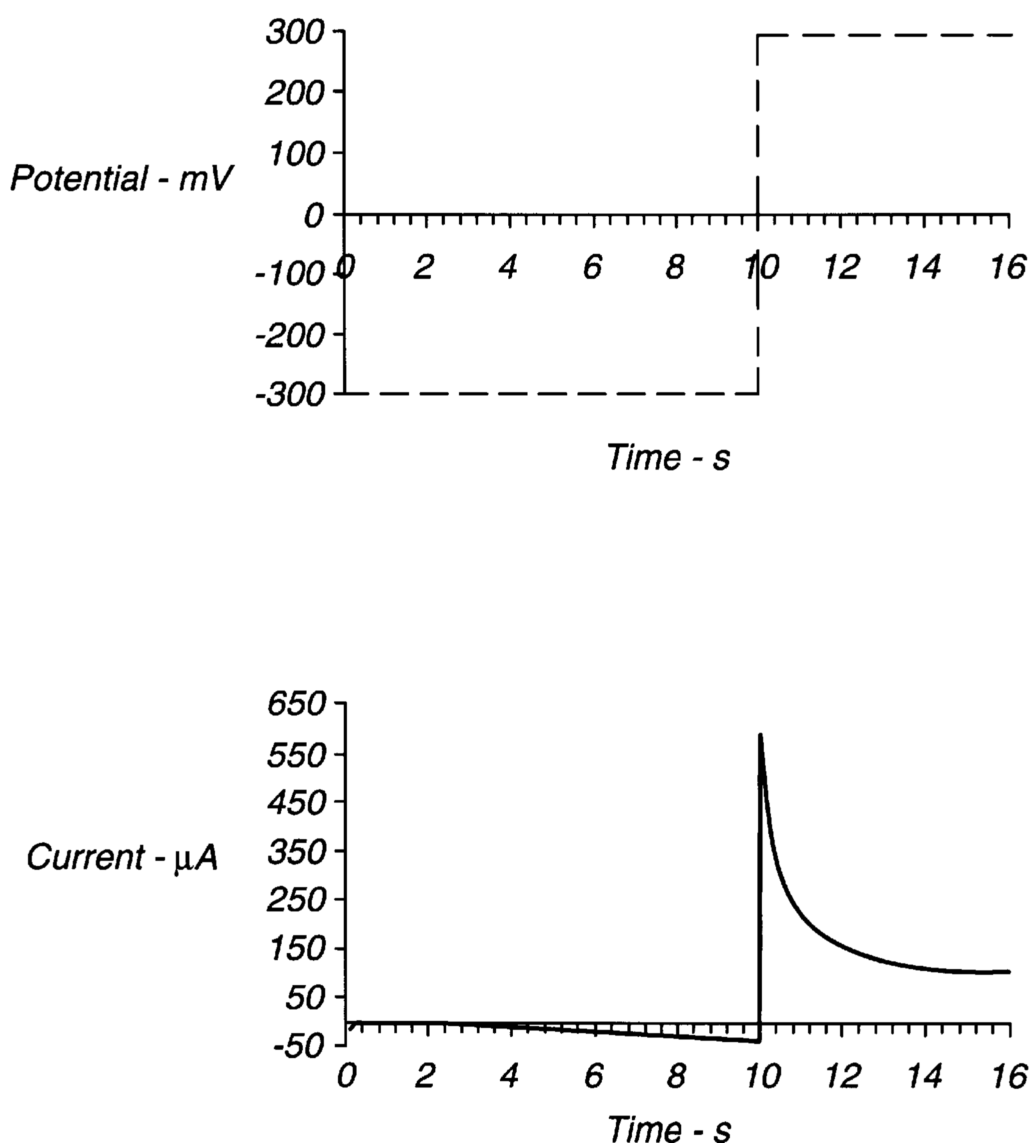
FIG. 3 is a graph of applied voltage and current response vs. time for an alternative assay method of the present invention.

FIG. 3 depicts a graph of the measured current and applied voltage vs. time in an alternative method. In this method, a second voltage pulse is applied across the electrodes after the predetermined time. Generally, the second pulse is applied immediately after the predetermined time (to minimize the total measurement time), but a delay is permissible. Again, reproducible results require reproducible procedures; thus, in this method as well, it is important to determine accurately the t=0 point. The second pulse causes a positive spike in the current through the electrodes, followed by a decaying current. The analyte concentration can, after the system has been calibrated, be determined from the decay rate, either alone or in combination with the current measurement depicted in FIG. 2. Generally, the current decays exponentially over a period that begins about 1 second after the second pulse is applied and continues for at least several seconds thereafter.

Figure 4:
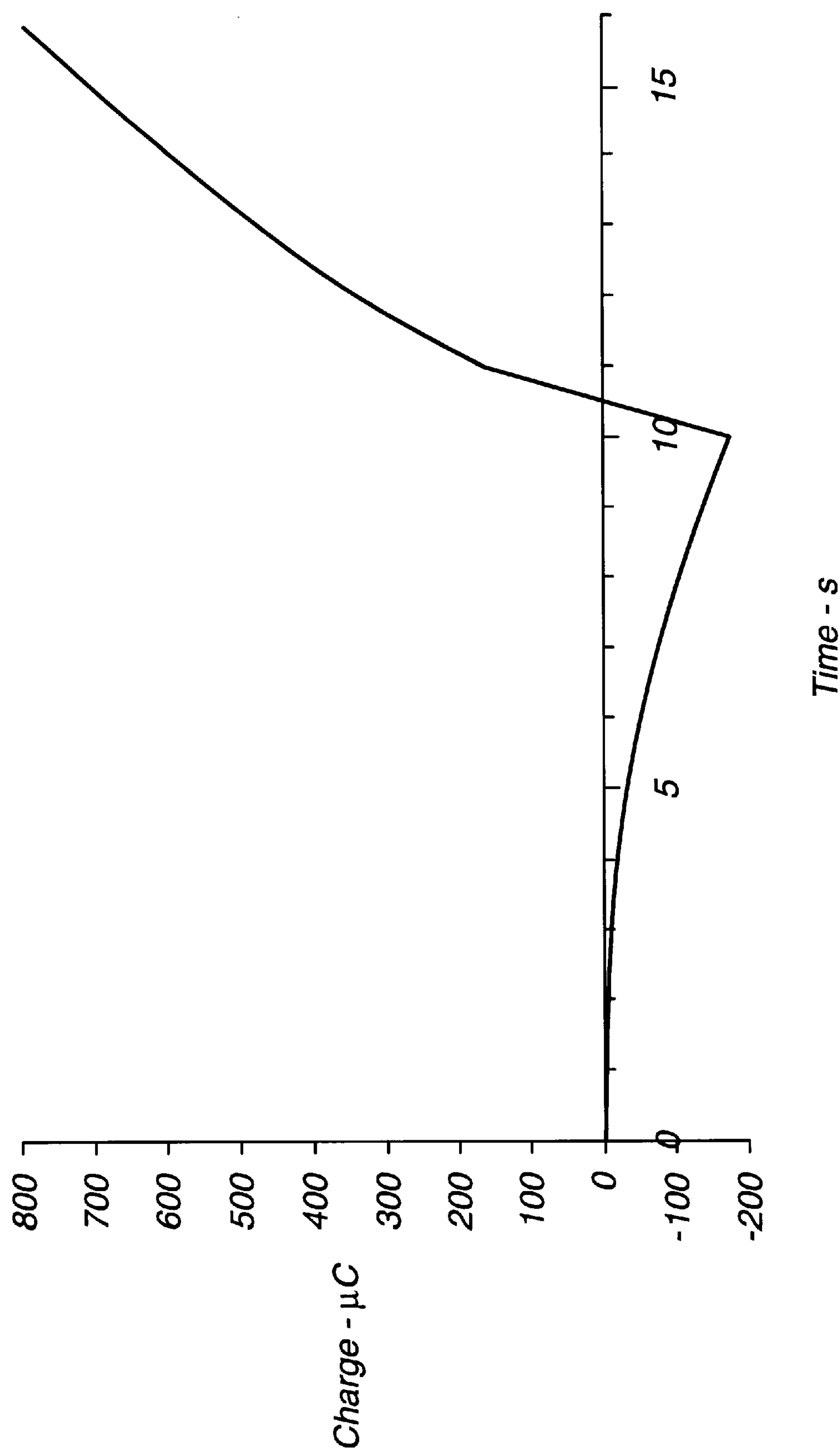
FIG. 4 is a graph of charge vs. time for another alternative assay method of the present invention.

FIG. 4 depicts the method of FIG. 3 in which charge, rather than current, was measured. As with the graph of FIG. 3, analyte concentration can be determined from the total charge at a fixed time and/or from the decay rate after the second voltage is applied.

Figure 5:
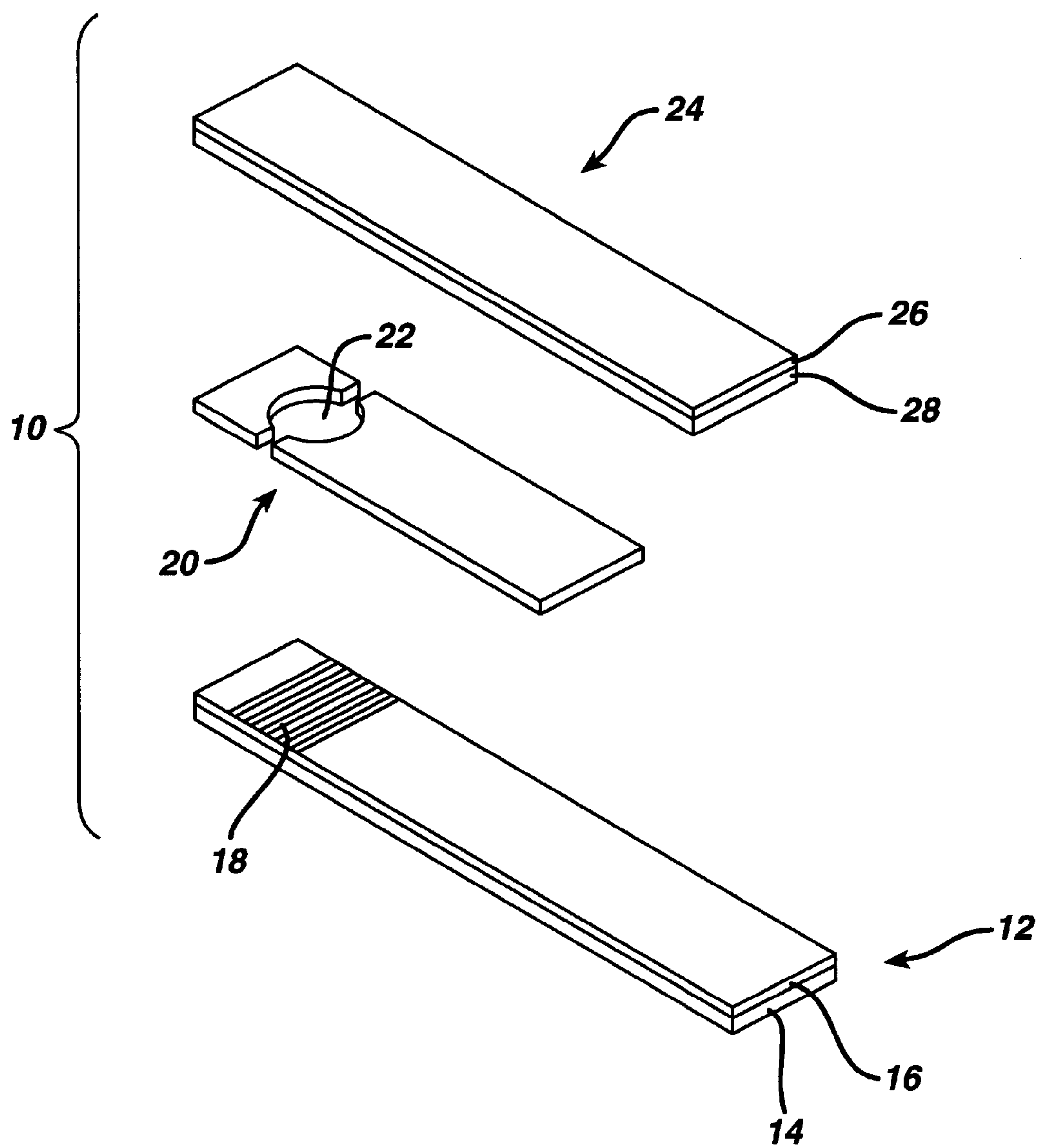
FIG. 5 depicts an electrochemical device suitable for use in the assay method of the present invention.

FIG. 5 depicts a "thin layer" device 10 that is suitable for use in the methods described above. Substrate 12 is a polyester base 14 on which has been deposited—typically, by sputtering—a Pd coating 16, which forms the working electrode. A dry reagent, consisting of buffer, mediator, and enzyme, is deposited near one end 18 of the electrode. Spacing layer 20 is double-sided adhesive having a cutout 22 that defines the electrochemical cell. Typically the spacer is less than about 200 $\mu$m thick. Top layer 24 is polyester layer 26 on which has been deposited—typically by sputtering, also—a Au coating 28, which forms the reference electrode.

A device of the type described above can use a glucose oxidase (GOD)/ferricyanide system to determine glucose concentrations via the following reactions, in which GOD* is the reduced enzyme.

Reaction 1 glucose+GOD→gluconic acid+GOD*

Reaction 2

GOD*+2ferricyanide→GOD+2ferrocyanide.

Ferricyanide ($[Fe(CN)_6]^{3-}$) is the mediator, which returns the GOD* to its catalytic state. GOD, an enzyme catalyst, will continue to oxidize glucose so long as excess mediator is present. Ferrocyanide ($[Fe(CN)_6]^{4-}$) is the product of the total reaction. Ideally, there is no ferrocyanide initially, although in practice there is often a small quantity. After the reaction is complete, the concentration of ferrocyanide (measured electrochemically) indicates the initial concentration of glucose. The total reaction is the sum of reactions 1 and 2.

Reaction 3 glucose+2ferricyanide→gluconic acid+2ferrocyanide

"Glucose" refers specifically to β-D-glucose.

Details of this system are described in PCT application no. WO 97/18465, incorporated herein by reference.

Figure 6:
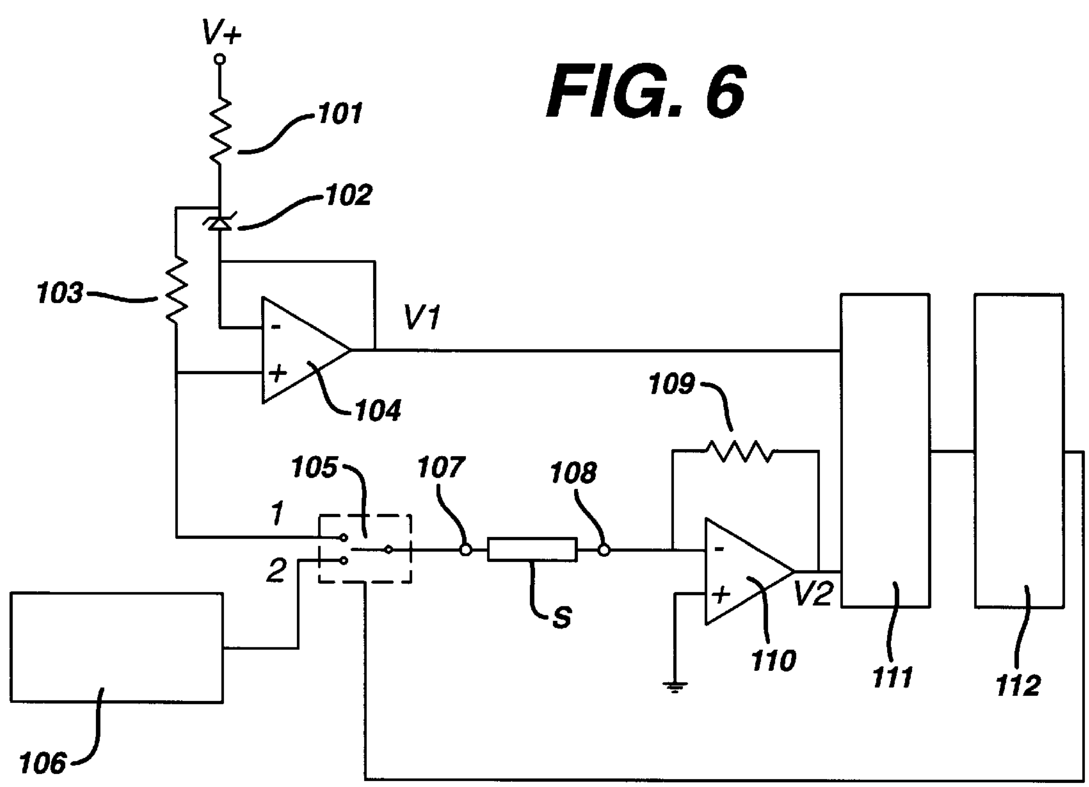
FIG. 6 is a diagram of a circuit suitable for use in the present invention.

FIG. 6 depicts an embodiment of suitable circuitry to practice this invention. Initially, a constant current source is applied to the strips with switch 105 in position 1. The current source consists of operational amplifier 104, voltage reference 102, and resistors 101 and 103. The current is determined by the ratio of voltage reference 102 to resistor 103. Resistor 101 is used to generate the required bias. Operational amplifier 110 and resistor 109 are used as a current-to-voltage converter. Initially, with no sample on the strip, the resistance between points 107 and 108 is very large, and the current passing through the strip is negligible. The output voltage of operational amplifier 104(V1) is high in this condition. When a sample is applied to the strip, its resistance drops significantly and, since a constant current flows through the strip, V1 drops. V1 is fed to microprocessor 112 through analog-to-digital converter 111. Microprocessor 112, recognizing this reduced voltage as sample detection, switches 105 to position 2 to disconnect the strip from the current source and connect it to the voltage source 106. In this condition, a chronoamperometric measurement can be achieved by measuring the output voltage of the operational amplifier 110 (V2). This voltage is proportional to the current passing through the strip.

The following Example demonstrates the present invention but is not intended to be in any way limiting.

EXAMPLE

The circuit of FIG. 6 was established, with strip S being a thin layer electrochemical glucose strip of the type shown in FIG. 5, having Pd and Au electrodes. The Pd electrode was coated with a layer of buffer, glucose dehydrogenase (PQQ), and ferricyanide. A constant, small (~1 $\mu$A) non-perturbing current was applied between the working electrode and counter/reference electrode of the dry glucose strip. Because the strip was dry, the resistance between the working and counter/reference electrode was essentially infinite. After a whole-blood sample was applied across the cell, a drop in voltage was observed. A threshold of about 50 to 500 mV initiated the start time (a threshold of about 300 mV is preferred). After sample was detected, the instrument switched from applying a constant current to applying a constant voltage. Measurement of the current through the sample as a function of time permitted the glucose concentration to be calculated.

It will be understood by those skilled in the art that the foregoing description and Example are illustrative of practicing the present invention, but are in no way limiting. Variations of the detail presented herein may be made, without departing from the scope and spirit of the present invention.

We claim:

1. A method for measuring an analyte concentration in a sample of a biological fluid that is applied to an electrochemical diagnostic strip of the type that includes juxtaposed working and reference electrodes comprising (a) applying a predetermined, constant current source between the working and reference electrodes, (b) monitoring a potential difference across the electrodes, (c) applying the sample to the strip, (d) determining a sample detection time by noting when the potential difference falls below a predetermined threshold voltage, (e) applying a predetermined constant voltage to the sample, (f) measuring an electrical response at a predetermined time after applying the constant voltage, and (g) calculating the analyte concentration using the measured electrical response.

2. The method of claim 1 in which the electrical response measured is current through the sample at the predetermined time.

3. The method of claim 1 in which the electrical response measured is charge passing through the sample from the sample detection time to the predetermined time.

4. The method of claim 1, further comprising applying a second predetermined voltage after the predetermined time and measuring a second electrical response after applying the second predetermined voltage.

5. The method of claim 4 in which the second electrical response is a rate of decay of current through the sample.

6. The method of claim 4 in which the second electrical response is charge passing through the sample during a predetermined time interval after the second voltage is applied.

7. A meter for measuring an analyte concentration in a sample of a biological fluid that has been applied between a working and reference electrode of a diagnostic strip comprising, in electrical communication, (a) means for applying a predetermined current between the working and reference electrodes, (b) means for monitoring a potential difference across the electrodes, (c) means for determining when the potential difference falls below a predetermined threshold voltage to indicate sample detection, (d) means responsive to sample detection for applying a predetermined constant voltage to the sample, (e) means for measuring a resulting electrical response, and (f) means for calculating the analyte concentration by using the measured electrical response.

8. The meter of claim 7 in which the means for measuring a resulting electrical response is an ammeter.

9. The meter of claim 7 in which the means for measuring a resulting electrical response is a coulometer.

10. The meter of claim 7 further comprising means for applying a second predetermined voltage to the sample and means for measuring a second resulting electrical response.

11. The meter of claim 10 in which the means for measuring a second resulting electrical response is an ammeter.

12. The meter of claim 10 in which the means for measuring a second resulting electrical response is a coulometer.

13. A method for measuring an analyte concentration in a sample of a biological fluid that is applied to an electrochemical diagnostic strip of the type that includes juxtaposed working and reference electrodes comprising (a) applying a predetermined, constant current source between the working and reference electrodes, (b) monitoring a potential difference across the electrodes, (c) applying the sample to the strip, (d) determining a sample detection time by noting when the potential difference falls below a predetermined threshold voltage, (e) applying a predetermined constant voltage to the sample, (f) applying a second predetermined voltage to the sample after a first predetermined time, (g) measuring an electrical response at a predetermined time after the first predetermined time, and (h) calculating the analyte concentration using the measured electrical response.

14. The method of claim 13 in which the electrical response measured is a rate of decay of current through the sample.

15. The method of claim 13 in which the electrical response measured is the charge passing through the sample during a predetermined time interval after the second predetermined voltage is applied.

* * * * *